(12) United States Patent
Schomacker et al.

(10) Patent No.: US 9,381,057 B2
(45) Date of Patent: Jul. 5, 2016

(54) REDUCTION OF RF ELECTRODE EDGE EFFECT

(71) Applicant: Candela Corporation, Wayland, MA (US)

(72) Inventors: Kevin T. Schomacker, Maynard, MA (US); Avner Rosenberg, Beit-Shearim (IL)

(73) Assignee: Candela Corporation, Wayland, MA (US)

( * ) Notice: Subject to any disclaimer, the term of this patent is extended or adjusted under 35 U.S.C. 154(b) by 0 days.

(21) Appl. No.: 14/566,777

(22) Filed: Dec. 11, 2014

(65) Prior Publication Data

US 2015/0201993 A1    Jul. 23, 2015

Related U.S. Application Data

(60) Division of application No. 13/494,319, filed on Jun. 12, 2012, now Pat. No. 9,277,958, which is a continuation-in-part of application No. 13/402,320, filed on Feb. 22, 2012.

(51) Int. Cl.

| | |
|---|---|
| *A61N 1/18* | (2006.01) |
| *A61B 18/14* | (2006.01) |
| *A61N 1/04* | (2006.01) |
| *A61B 18/20* | (2006.01) |
| *A61N 1/28* | (2006.01) |
| *A61N 5/06* | (2006.01) |
| *A61N 1/06* | (2006.01) |

(Continued)

(52) U.S. Cl.
CPC ............... *A61B 18/14* (2013.01); *A61B 18/20* (2013.01); *A61N 1/0408* (2013.01); *A61N 1/0472* (2013.01); *A61N 1/28* (2013.01); *A61N 5/0613* (2013.01); *A61B 2018/00452* (2013.01); *A61B 2018/2035* (2013.01); *A61N 1/06* (2013.01); *A61N 1/328* (2013.01)

(58) Field of Classification Search
CPC ...... A61N 1/04; A61N 1/0404; A61N 1/0408; A61N 1/328; A61N 1/06
See application file for complete search history.

(56) References Cited

U.S. PATENT DOCUMENTS

| 5,334,551 | A  * | 8/1994 | Komatsu ..................... 438/31 |
| 6,350,276 | B1 * | 2/2002 | Knowlton ................... 607/104 |

(Continued)

FOREIGN PATENT DOCUMENTS

WO    03053266 A2    7/2003

OTHER PUBLICATIONS

European Search Report in EP 13155133.5 dated Jul. 10, 2013.

*Primary Examiner* — Kaitlyn Smith
(74) *Attorney, Agent, or Firm* — Manelli Selter PLLC; Edward J. Stemberger

(57) ABSTRACT

A skin surface is treated with RF energy (e.g., unipolar, monopolar, bipolar or multipolar RF delivery). A first semiconductive cap disposed on a first distal end of a first electrode and, optionally, a second semiconductive cap disposed on a second distal end of a second electrode are applied to the skin surface. RF energy is delivered from the first electrode and the second electrode through the first semiconductive cap and the second semiconductive cap, respectively, through the skin surface. The first semiconductive cap and/or the second semiconductive cap have an electrical conductivity matched or substantially matched to the skin's electrical conductivity (e.g., about 0.1 to about 2 times that of the skin).

11 Claims, 14 Drawing Sheets

(51) Int. Cl.
  *A61N 1/32* (2006.01)
  *A61B 18/00* (2006.01)

(56) References Cited

U.S. PATENT DOCUMENTS

| | | | |
|---|---|---|---|
| 6,413,255 B1 | 7/2002 | Stern | |
| 6,483,690 B1* | 11/2002 | Nakajima et al. | 361/234 |
| 2004/0206365 A1* | 10/2004 | Knowlton | 128/898 |
| 2006/0036300 A1* | 2/2006 | Kreindel | 607/99 |
| 2007/0083247 A1* | 4/2007 | Wyeth et al. | 607/99 |
| 2008/0097557 A1* | 4/2008 | Eggers et al. | 607/99 |
| 2009/0082764 A1 | 3/2009 | Knowlton et al. | |
| 2010/0016703 A1* | 1/2010 | Batkin et al. | 600/392 |
| 2010/0312314 A1* | 12/2010 | Ice et al. | 607/100 |

* cited by examiner

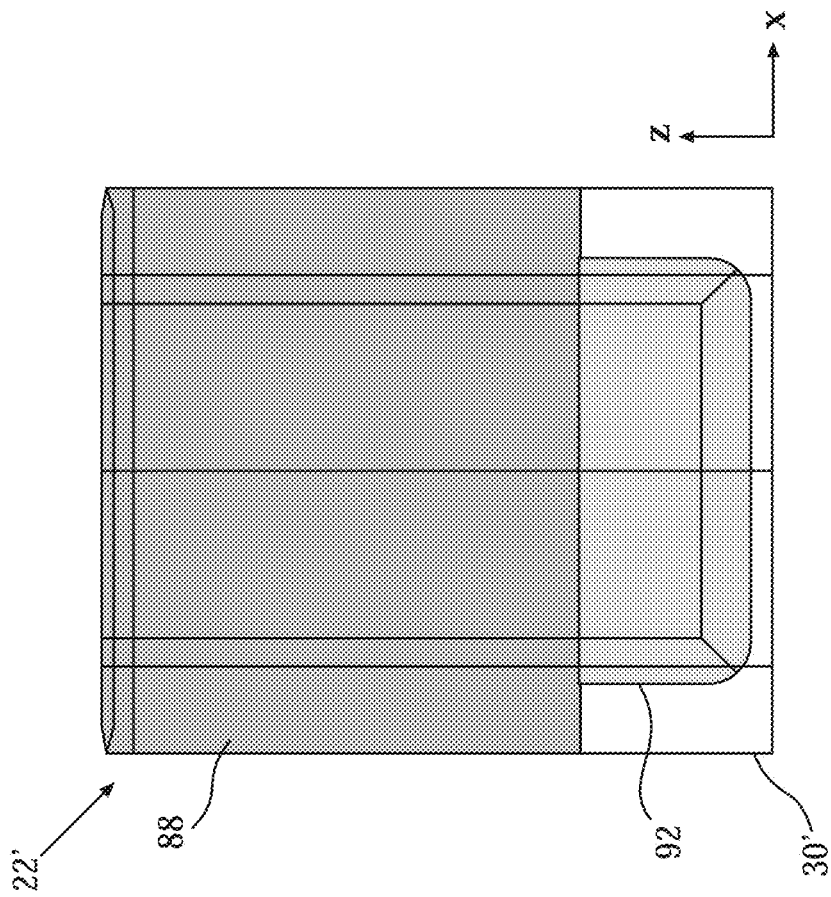
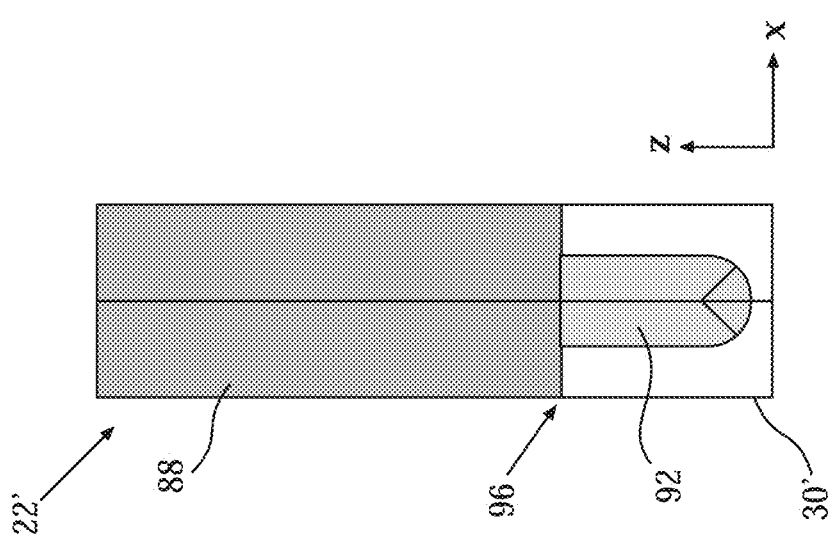
FIGURE 8B
FIGURE 8A

REDUCTION OF RF ELECTRODE EDGE EFFECT

CROSS REFERENCE TO RELATED APPLICATIONS

This application is a divisional of U.S. patent application Ser. No. 13/494,319, now U.S. Pat. No. 9,277,958 filed Jun. 12, 2012, which is a continuation-in-part of U.S. patent application Ser. No. 13/402,320 filed Feb. 22, 2012, the entire disclosures of which are herein incorporated by reference.

FIELD OF THE INVENTION

The invention relates generally to radio frequency (RF) energy treatment devices, and more particularly, to improving the delivery of RF electrical energy to tissue by reducing edge effects and improving the spatial uniformity of energy delivered to skin or other tissues.

BACKGROUND

Many aesthetic dermatologic procedures resort to delivering thermal energy to skin or underlying subcutaneous tissue as a means to stimulate a therapeutic effect. Procedures such as skin resurfacing, skin tightening, wrinkle reduction, hair reduction, tattoo removal, body contouring, and treatments for excessive sweating, sebaceous gland production, acne, pigmented lesions, vascular lesions and blood vessels take advantage of heat to achieve a desired effect. Many different technologies can be used to heat the skin and/or underlying tissues including lasers, incoherent light sources, radiofrequency electrical energy sources, and ultrasound energy sources.

A problem with delivering RF energy to tissue is the fundamental concentration of current density along the edges of the electrode in contact with tissue. For monopolar RF energy delivery, higher skin surface temperatures occur along the entire perimeter of the electrode. For bipolar RF energy delivery, the concentration of current also occurs along the edges, but even higher current densities occur along the inner two edges forming the gap between the two electrodes having the shortest electrical path. These non-uniform thermal effects limit the amount of energy that can be delivered to tissue so as to avoid adverse skin effects such as burns, blisters, and erythema.

SUMMARY OF THE INVENTION

The invention, in various embodiments, features a method and apparatus that uses a semiconductive material applied to an electrode that optimizes electrical energy delivered to tissue while minimizing thermal hotspots around edge of the electrode. The semiconductive material need not be specific to semiconductors typically used in electronic components (e.g., silicon, germanium, gallium arsenide, etc.), but can refer more generally to any material whose conductivity lies between conductors and insulators (typically between $10^3$ to $10^{-8}$ S/m).

The semiconductive material can be a ceramic material. The semiconductive material can have a specified electrical conductivity to improve the spatial uniformity of energy delivered to skin or other tissues and a specified thermal conductivity so that heat at the metal electrode-ceramic junction is carried away via a heat sink and does not accumulate causing unwanted skin surface heating. The semiconductive material can have an electrical conductivity matched or substantially matched to the skin's electrical conductivity (e.g., about 0.1 to about 2 times that of the skin). In addition, the ceramic can have a low coefficient of thermal expansion and be relatively scratch resistant. The semiconductive material can have an electrical conductivity of about 0.03 S/m to about 3.0 S/m (e.g., about 0.03 S/m to about 0.3 S/m) and a thermal conductivity of about 5 W/m·° C. to about 500 W/m·° C.

The semiconductive material can be a cap on the electrode, and can have a geometric shape that facilitates relocation of hotspots to reduce or eliminate thermal damage by the electrode. The semiconductive material can be graded to be thicker at the edges of the electrode than in the center. In certain embodiments (e.g., unipolar, monopolar, bipolar or multipolar RF delivery), the cap can have a trapezoidal vertical cross-section so that the thermal hot spot occurs inside the cap. In various embodiments, the ceramic can be asymmetric so that it is thicker along its inner edge compared to its outer edge. The inner edge is the edge adjacent to the next closest electrode.

In one aspect, there is an applicator for RF energy delivered through a skin surface. The applicator includes a base, a first electrode connected to the base, and a first semiconductive cap disposed on a first distal end of the first electrode. The first electrode extends from the base toward a first location of the skin surface. The first semiconductive cap is configured to contact the first location of the skin surface. The RF energy is delivered from the first electrode through the first semiconductive cap through the skin surface. In certain embodiments, the applicator includes a second electrode connected to the base and a second semiconductive cap disposed on a second distal end of the second electrode. The second electrode extends from the base toward a second location of the skin surface. The second electrode is laterally offset from the first electrode along the skin surface. The second semiconductive cap is configured to contact the second location of the skin surface. The RF energy is delivered from the first electrode and the second electrode through the first semiconductive cap and the second semiconductive cap, respectively, through the skin surface. The RF energy delivered by the first electrode can have opposite phase to the RF energy delivered by the second electrode.

In another aspect, there is a method of treating a skin surface with RF energy. The method includes applying to the skin surface a first semiconductive cap disposed on a first distal end of a first electrode and delivering RF energy from the first electrode through the first semiconductive cap through the skin surface. In some embodiments, the method includes applying to the skin surface a second semiconductive cap disposed on a second distal end of a second electrode and delivering RF energy from the first electrode and the second electrode through the first semiconductive cap and the second semiconductive cap, respectively, through the skin surface.

In still another aspect, there is an apparatus for treating a skin surface with RF energy. The apparatus include means for applying to the skin surface a first semiconductive cap disposed on a first distal end of a first electrode and means for delivering RF energy from the first electrode through the first semiconductive cap through the skin surface. In some embodiments, the apparatus includes means for applying to the skin surface a second semiconductive cap disposed on a second distal end of a second electrode and means for delivering RF energy from the first electrode and the second electrode through the first semiconductive cap and the second semiconductive cap, respectively, through the skin surface.

In other examples, any of the aspects above, or any apparatus, system or device, or method, process or technique, described herein, can include one or more of the following features.

In various embodiments, the source provides monopolar RF energy or bipolar RF energy. The RF energy can have a frequency of about 100 kHz to about 10 MHz (e.g., about 1 MHz). The source can provide the RF energy at about 10 J/cm$^3$ to about 500 J/cm$^3$ (e.g., about 50 J/cm$^3$ to about 120 J/cm$^3$). The source can provide the RF energy in pulses of about 0.1 second to about 1 second.

In various embodiments, the electrical conductivity of each semiconductive cap is matched or substantially matched to the conductivity of the skin (e.g., 0.1 to about 2 times that of skin at the frequency of interest). The electrical conductivity of each semiconductive cap can be matched so that about 5% to about 30% (e.g., about 10%) of the RF energy is lost to the semiconductive cap. The first semiconductive cap and/or the second semiconductive cap can have an electrical conductivity of about 0.03 S/m to about 3.0 S/m (e.g., 0.11 S/m). The thermal conductivity can be about 5 W/m·° C. to about 500 W/m·° C. or about 50 W/m·° C. to about 250 W/m·° C.

In certain embodiments, the first semiconductive cap and/or the second semiconductive cap has/have a trapezoidal vertical cross-section including a first surface and a second surface parallel or substantially parallel to the first surface. The first surface adjoins the first electrode, and the second surface is configured to contact the first location of the skin surface. The trapezoidal vertical cross-section can be an isosceles trapezoidal vertical cross-section. A cap can include a third surface forming an obtuse angle with the first surface so that the second surface is longer than the first surface.

In various embodiments, each semiconductive cap tapers from an inner edge to the center. The thickness of each semiconductive cap between the blunt surface and the curved surface can be thickest at the inner portion, thinnest at the center portion, and thicker than the center portion but thinner than the inner portion at an outer portion.

In various embodiments, each semiconductive cap tapers from an inner edge to the center. The thickness of each semiconductive cap between the blunt surface and the curved surface can be thickest at the inner portion and thinner at the center portion and outer portion.

In various embodiments, each semiconductive cap can extend along the skin surface beyond the electrode such that the extension tapers towards the inner edge.

In various embodiments, each semiconductive cap includes a semiconductive ceramic. Each semiconductive cap can include a conductive silicon carbide based ceramic doped with a nonconductive material and/or a nonconductive aluminum nitride based ceramic doped with a conductive material. In certain embodiments, each semiconductive cap is affixed to the respective electrode with a conductive epoxy. In certain embodiments, each semiconductive cap is metalized so that the semiconductive cap can be soldered or brazed to the electrode.

In certain embodiments, the applicator can include a waveguide disposed between the first electrode and the second electrode to deliver optical radiation. The third surface of a semiconductive cap can abut a surface of the waveguide. The applicator can include one or more electrically insulating regions having a triangular vertical cross section disposed between a surface of the waveguide and one of the semiconductive caps.

Other aspects and advantages of the invention will become apparent from the following detailed description, taken in conjunction with the accompanying drawings, illustrating the principles of the invention by way of example only.

BRIEF DESCRIPTION OF THE DRAWINGS

The advantages of the invention described above, together with further advantages, may be better understood by referring to the following description taken in conjunction with the accompanying drawings. The drawings are not necessarily to scale, emphasis instead generally being placed upon illustrating the principles of the invention.

FIG. 8A shows a perspective view of another electrode and semiconductive cap embodiment.

FIG. 8B shows a side view of the embodiment shown in FIG. 7A.

DESCRIPTION OF THE INVENTION

Figure 1:
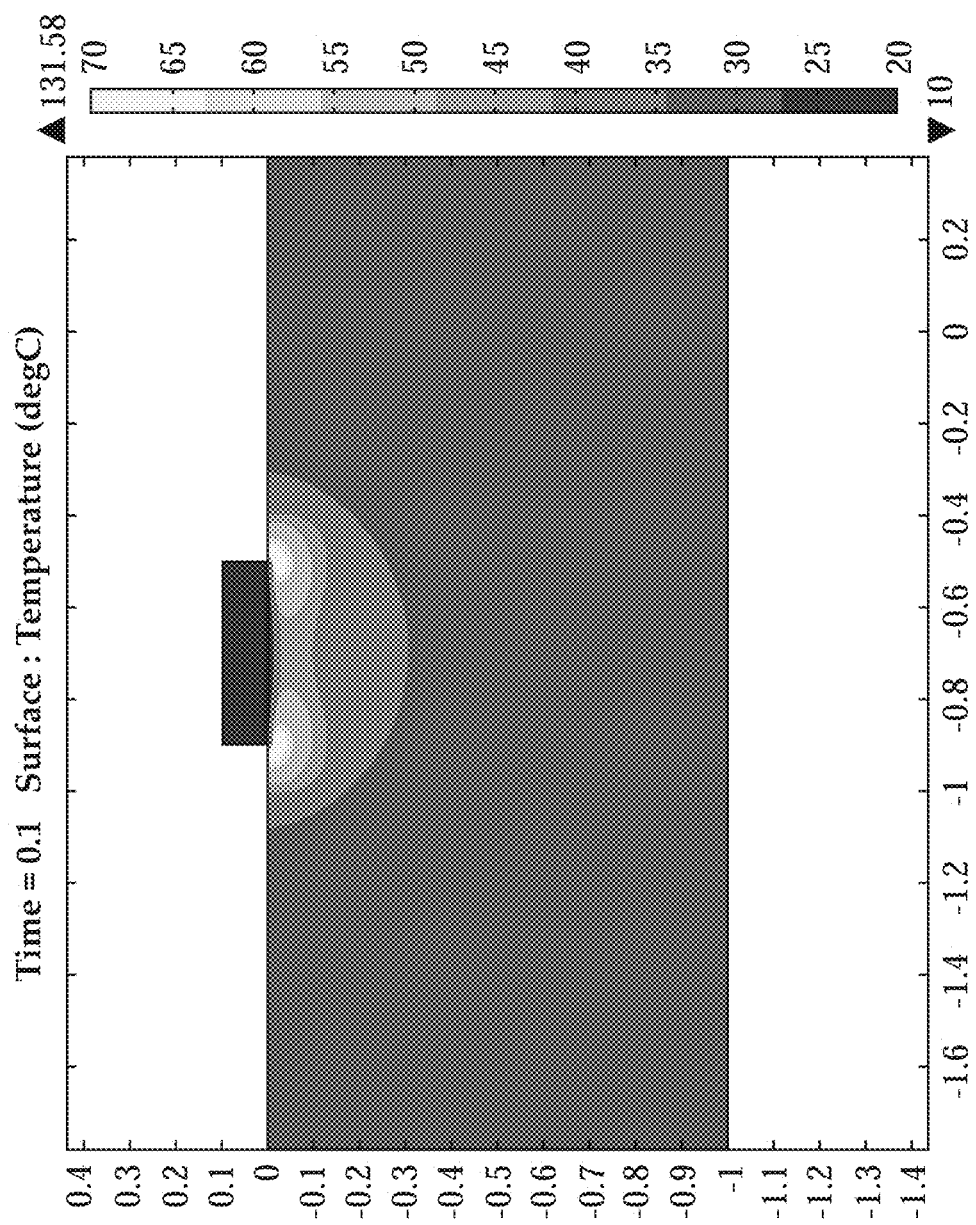
FIG. 1 shows a cross-section of a temperature profile in skin for a monopolar copper electrode applied to a skin surface without a semiconductive cap.
Figure 2:
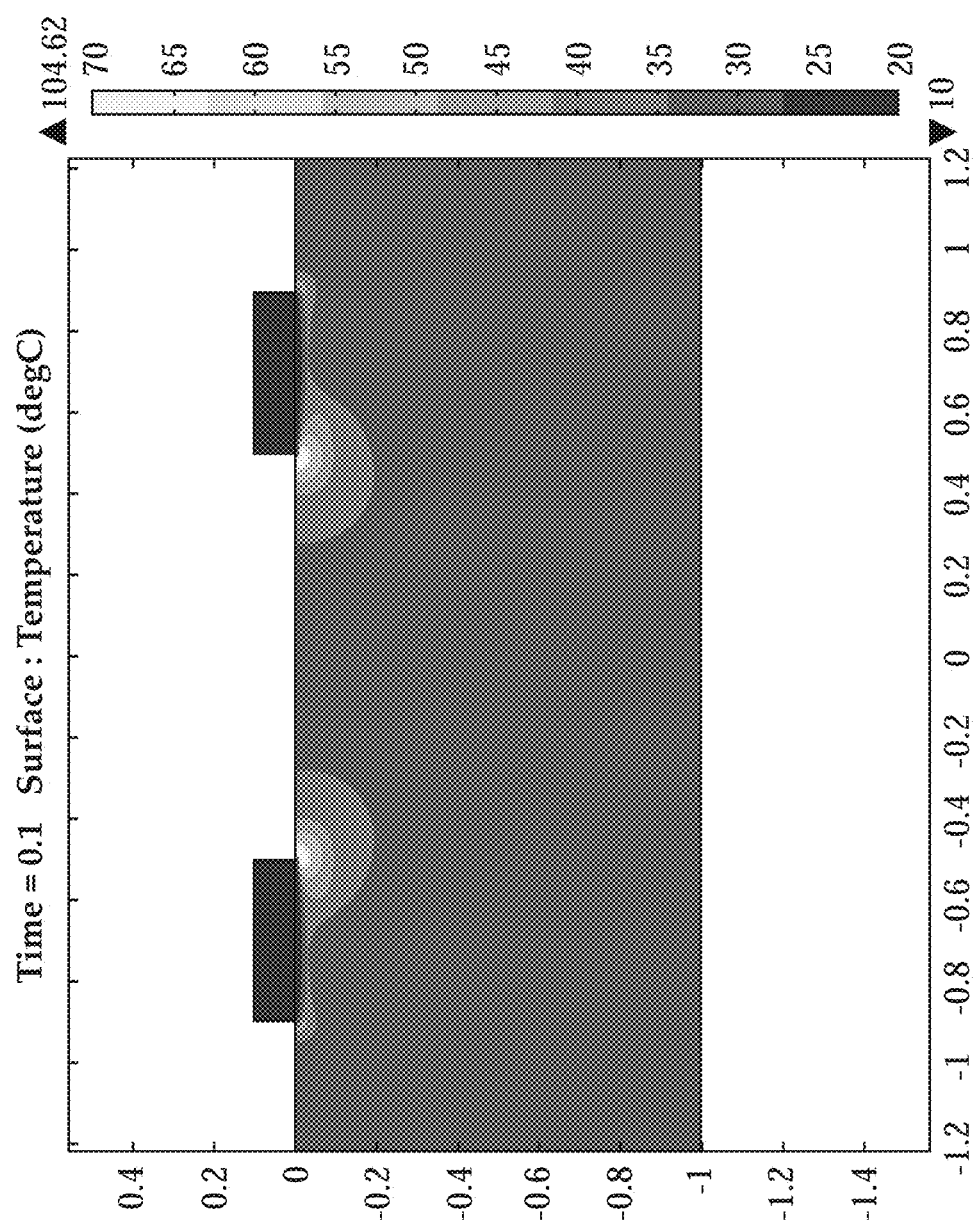
FIG. 2 shows a cross-section of a temperature profile in skin for bipolar copper electrodes applied to a skin surface without semiconductive caps.

FIG. 1 shows a cross-section of a temperature profile in skin for a monopolar copper electrode applied to a skin surface without a semiconductive cap. FIG. 2 shows a cross-section of a temperature profile in skin for bipolar copper electrodes applied to a skin surface without semiconductive caps. Uneven heat distribution is seen at the edges of the monopolar electrode and is symmetric (equal at both edges). For the bipolar electrodes, the uneven heat distribution is seen at the edges, but is asymmetric. The current density is greater along the inner electrode edges because the pathlength is shorter and hence impedance is lower. More current will travel this path. In both examples, 20 joules of RF energy is delivered to tissue. In general, temperatures greater than 70° C. lead to adverse skin effects such as blisters.

Figure 3:
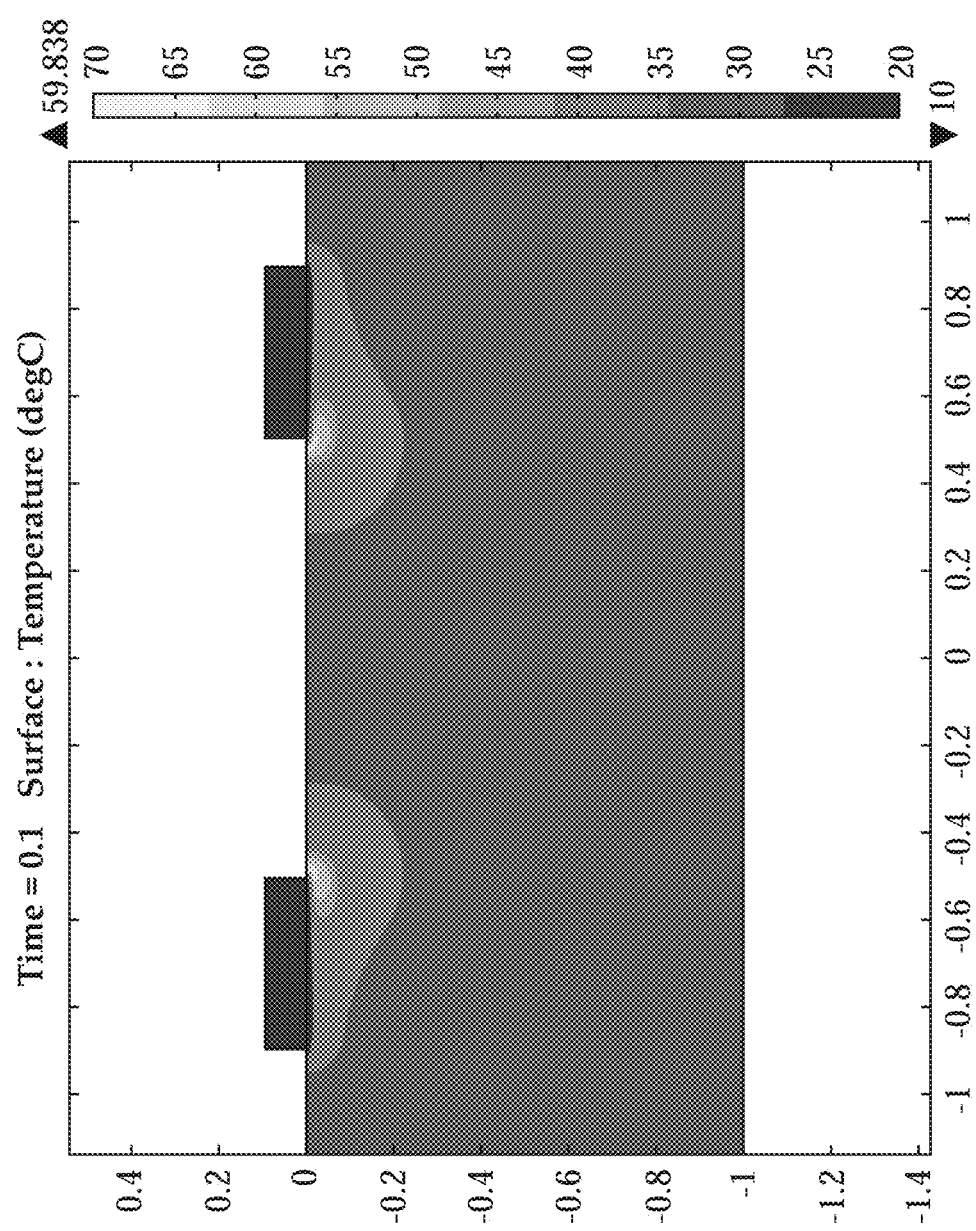
FIG. 3 shows a cross-section of a temperature profile in skin when using semiconductive caps on the electrodes.

FIG. 3 shows a cross-section of a temperature profile in skin when using semiconductive caps (e.g., formed from a ceramic material) on the electrodes. In the figure, the caps are illustrated, but the electrodes are not. The energy delivered to tissue is 20 joules, the same as was used in FIG. 2, but because the impedance between the cap and the tissue is better matched, the thermal hotspot is smaller. The hotspots appear on the inner edges due to the shorter electrical pathlength to the next adjacent electrode. High current densities also exist at the edge of the copper electrode-ceramic cap junction. Because of the high thermal conductivity of ceramic, heat at this junction is effectively conducted towards the electrode, so this density does not cause thermal hotspots at this junction and prevents overheating on the cap which is in contact with the skin.

Figure 4:
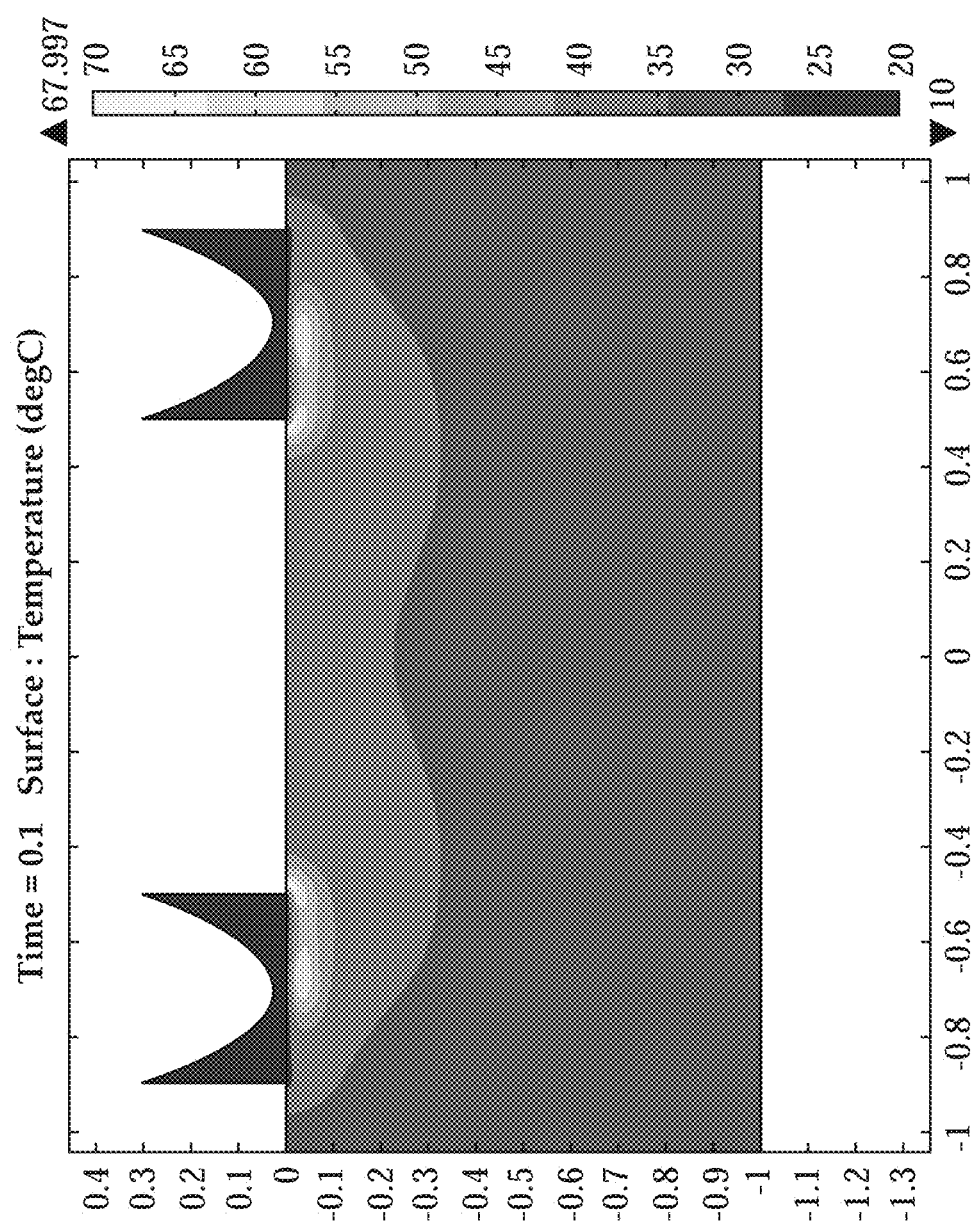
FIG. 4 shows a cross-section of a temperature profile in skin when using semiconductive caps having a variable thickness.

FIG. 4 shows a cross-section of a temperature profile in skin when using semiconductive caps with a variable thickness. In the figure, the caps are illustrated, but the electrodes are not. Because ceramic has finite impedance, it can be shaped to be thicker at the edges to further minimize the thermal hotspot on the inner edges causes by the shorter electrical pathlength. In this case, two times more energy or 40 Joules is delivered to skin, but the thermal hotspots are about half what is seen without the ceramic cap and more importantly less than the 70° C. critical temperature. In this case, the temperature of skin (1 mm deep, halfway between electrodes) is increased to about 42.8° C., an increase of about 10.8 degrees over the starting temperature of about 32° C. Without the ceramic cap, the increase is about 36.2° C. or only about 4.2 degrees above the initial temperature. So with the cap, the skin is more effectively heated with less risk of adverse effects to the skin surface underneath the electrodes.

Figure 5:
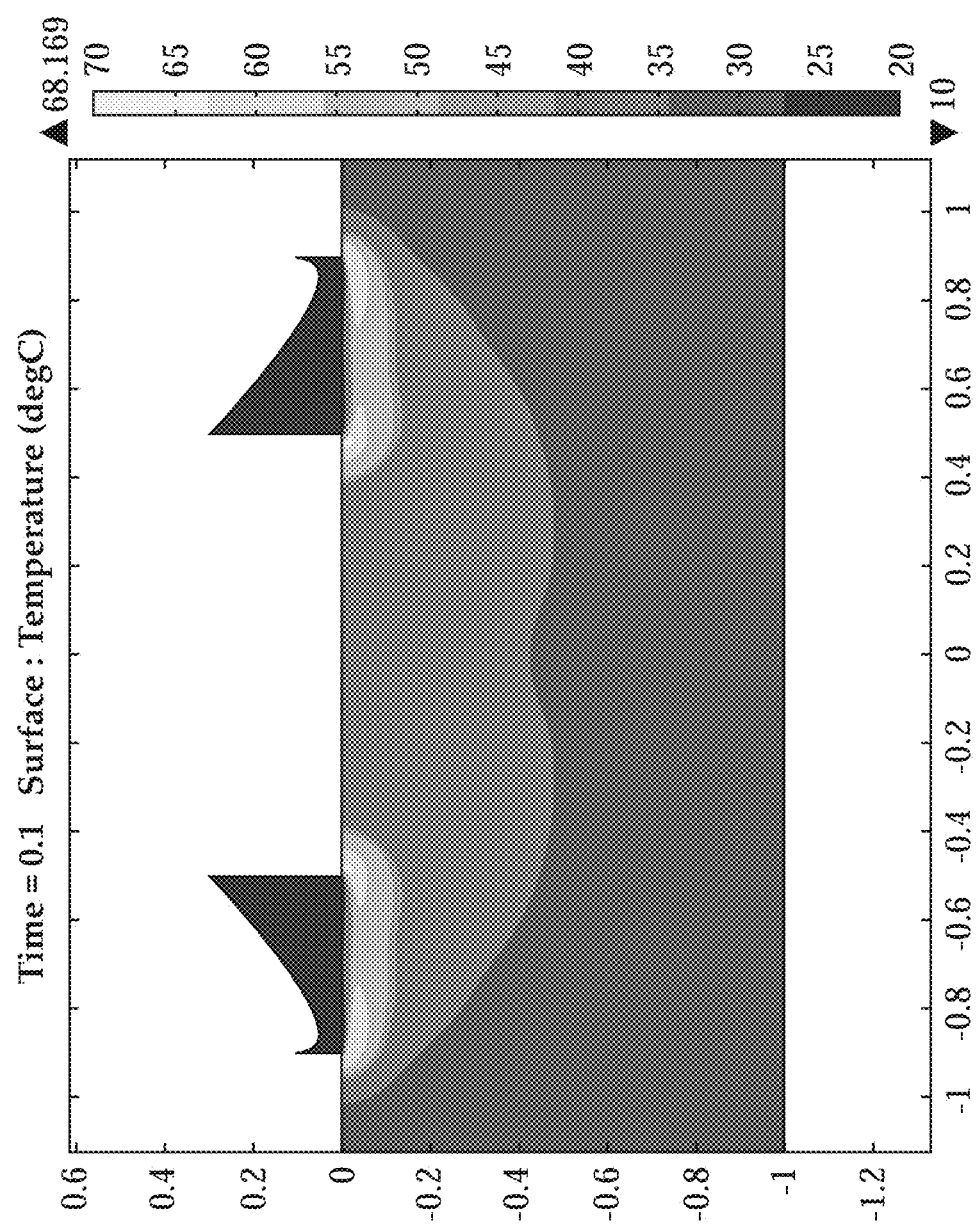
FIG. 5 shows a cross-section of another temperature profile in skin when using semiconductive caps with a variable thickness.

FIG. 5 shows a cross-section of a temperature profile in skin when using semiconductive caps with a variable thickness. In the figure, the caps are illustrated, but the electrodes are not. Each cap has a blunt surface in contact with the skin and a curved surface contacting the electrode. Each cap is asymmetric, being thickest at the inner portion, thinnest at the center portion, and thicker than the center portion but thinner than the inner portion at an outer portion. In the center portion, the cap tapers from thicker than the outer portion to thinner than the outer portion. In this case, 48 Joules of RF energy is delivered, but the thermal hotspots remain under 70° C. The temperature of skin (1 mm deep, halfway between electrodes) is increased to about 40° C. or an increase of about 8° C. Compared with the bare copper electrode, the mid-dermal increase is two times higher while the electrode hotspots are two times lower. In this configuration, a larger volume of tissue is heated compared to the previous configuration so the change in temperature is not as high even through more energy is being delivered to tissue.

Figure 6:
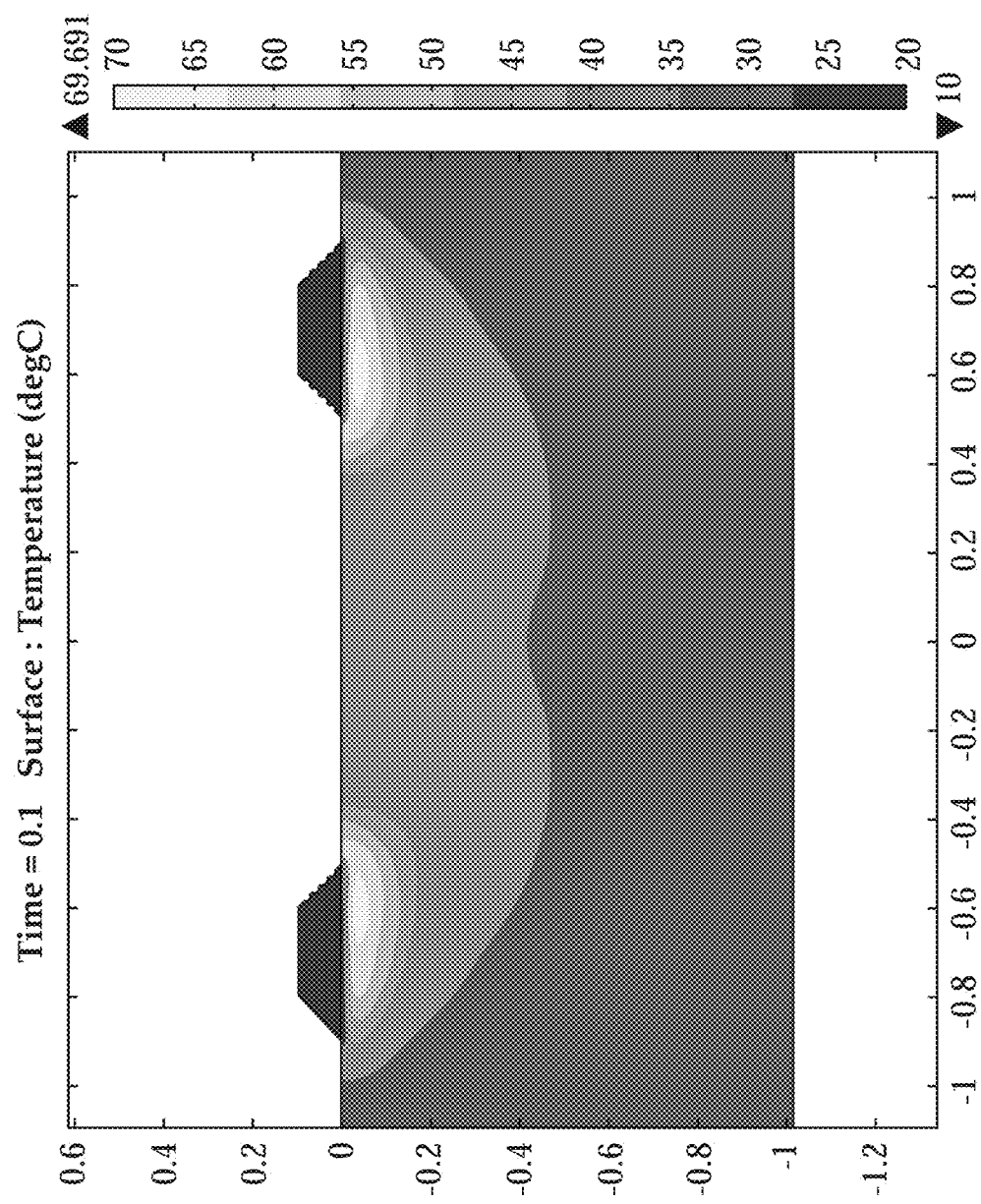
FIG. 6 shows a cross-section of another temperature profile in skin when using semiconductive caps having a trapezoidal cross-section.

FIG. 6 shows a cross-section of a temperature profile in skin when using trapezoidal semiconductive caps. In the figure, the caps are illustrated, but the electrodes are not. Each cap has a first surface and a second surface parallel to the first surface wherein the first surface adjoins the first electrode and the second surface is configured to contact the skin surface. In this case, 44 Joules of RF energy is delivered, and the thermal hotspots remain under 70° C. The temperature of skin (1 mm deep, halfway between electrodes) is increased to about 39.6° C. or an increase of about 7.6° C. Compared with the bare copper electrode, the mid-dermal increase is two times higher while the electrode hotspots are two times lower. In this configuration, a larger volume of tissue is heated compared to the configuration used in FIG. 4 so the change in temperature is not as high even through more energy is being delivered to tissue. Unlike the previous configurations, more RF energy will be lost to the semiconductive caps. RF loss to the ceramic caps is, in this case, about 30%. In FIGS. 5 and 6, the conductivity of the cap was about 0.11 S/m, about half that of skin.

Figure 7A:
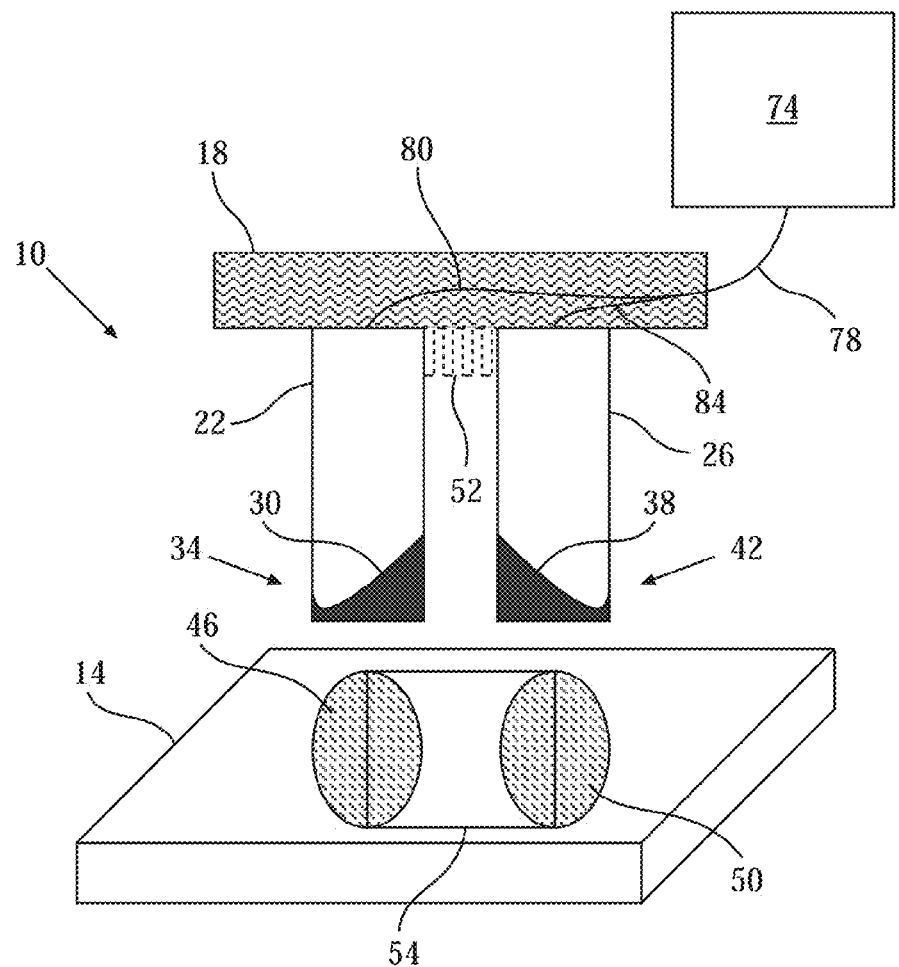
FIG. 7A shows a sectional view of an applicator for RF energy delivered through a skin surface.

FIG. 7A shows an applicator 10 for bipolar RF energy delivered through a skin surface 14. The applicator 10 includes a base 18, a first electrode 22 connected to the base 18, a second electrode 26 connected to the base 18, a first semiconductive cap 30 disposed on a first distal end 34 of the first electrode 22, a second semiconductive cap 38 disposed on a second distal 42 end of the second electrode 26. The first electrode 22 extends from the base 18 toward a first location 46 of the skin surface 14. The second electrode 26 extends from the base 18 toward a second location 50 of the skin surface 14. The first electrode 22 is laterally offset along the skin surface 14 from the second electrode 26, and the current through the first electrode 22 and the second electrode 26 have opposite phases. Each electrode 22 or 26 can be cooled to about 10° C. using a thermoelectric cooler 52 attached to the side of the electrode and or the base 18. Each electrode 22 or 26 can have separate thermoelectric coolers 52, which can be water or air cooled.

Base 18 can be any member to which the electrodes 22 and 26 are attachable. In some embodiments, base 18 is modular and includes separate members for connection to electrodes 22 and 26. Base 18 can be a portion or section of a hand piece or applicator, or can be the hand piece or applicator. In some embodiments, base 18 and electrodes 22 and 26 are integrally formed.

Each electrode 22 or 26 and/or each semiconductive cap 30 or 38 can have an elliptical shape so that the footprints 46 and 50 of the caps 30 and 38 are elliptical or oval in shape. The treatment region 54 formed by the electrodes 22 and 26 and/or semiconductive caps 30 and 38 can be rectangular in shape, and can extend into the skin surface to a predetermined depth.

Figures 7B, 7C:
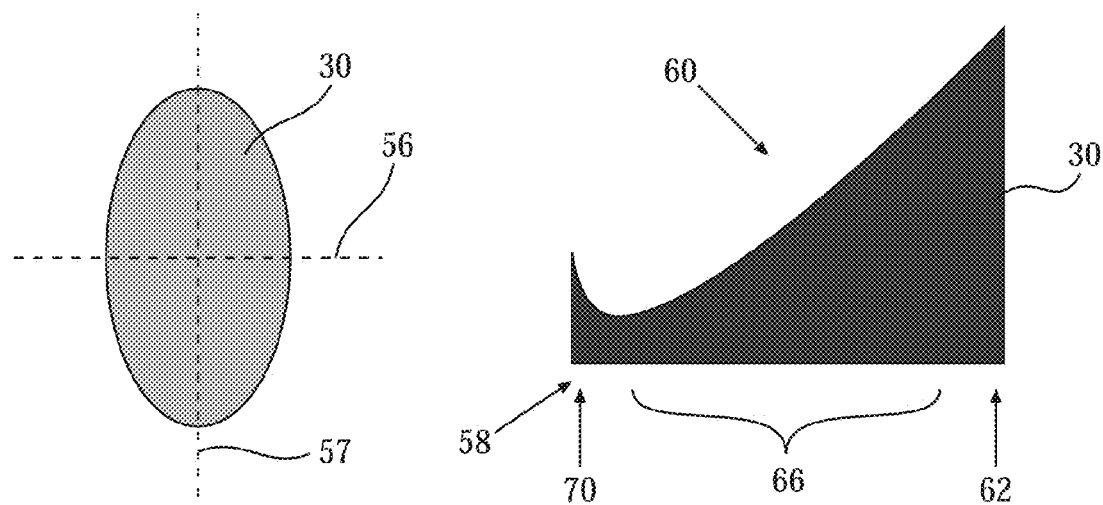
FIG. 7B shows a sectional view of a semiconductive cap for an electrode.
FIG. 7C shows a side elevation view of a semiconductive cap for an electrode.

FIG. 7B shows a sectional view of a semiconductive cap 30 (or 38) for an electrode 22 (or 26). In one example, each electrode 22 (or 26) and each semiconductive cap 30 (or 38) is about 4 mm wide at axis 56 and 12 mm deep at axis 57. Each electrode 22 or 26 can be about 4 to 15 mm long (e.g., about 12 mm long). The electrodes can be spaced apart by about 5 to 20 mm (e.g., about 12 mm or about 13 mm from inner edge to inner edge).

Each electrode 22 or 26 can be an electrically conductive metal (e.g., copper) or ceramic material. Each electrode 22 or 26 can be plated with a nonoxidizing surface such as chrome. Each electrode can be formed from a semiconductive ceramic with an appropriately shaped solder pad.

FIG. 7C shows a side elevation view through axis 56 of a semiconductive cap 30 (or 38) for an electrode 22 (or 26). The semiconductive cap 30 (or 38) has a blunt surface 58 adapted to contact a location of the skin surface 14 (e.g., the first location 46 if it is the first semiconductive cap 30 and the second location 50 if it is the second semiconductive cap 38). The semiconductive cap 30 (or 38) has a curved surface 60 that can be affixed to the first electrode 22 (or the second electrode 26). The thickness of each semiconductive cap 30 (or 38) between the blunt surface 58 and the curved surface 60 can be tapered or graded from the inner edge to the outer edge. The semiconductive cap 30 (or 38) can be thicker at an inner portion 62 and thinner at a center portion 66 to homogenize the electrical field at the skin surface 14. An outer portion 70 of the semiconductive cap 30 (or 38) can be thicker than the center portion 66 but thinner than the inner portion 62. In this way, the entrance or exit point for current entering or leaving the electrode is spread across the entire cap surface, which homogenizes the tissue entry current field. The inner edge or portion is the edge/portion adjacent to the next closest electrode.

In certain embodiments, along axis 56, the inner portion 62 is about 2 mm thick, the center portion 66 is about 0.5 mm thick, and the outer portion 70 is about 1 mm. Along axis 57, the center is about 1 mm thick and the upper and lower edges are about 3 mm thick.

Referring back to FIG. 7A, a source 74 of RF energy is in electrical communication with the base 18 via cable 78, which can include a single wire or a bundle of wires. Each electrode 22 and 26 includes a separate wire feed 80 and 84, respectively. Wire feeds 80 and 84 can be in electrical communication with separate wires or feeds of cable 78. Source 74 can deliver RF energy to and through the skin surface 14. The source 74 can deliver RF energy via cable 78 to wire feed 80 and 84 to the first electrode 22 and the second electrode 26, respectively. RF energy can be delivered from the first electrode 22 and the second electrode 26 through the first semiconductive cap 30 and the second semiconductive cap 30, respectively, through the skin surface 14.

The electrical conductivity of the semiconductive material (e.g., the ceramic material) can be approximate to the electrical conductivity of skin at the tissue-electrode interface. In certain embodiments, the conductivity of each semiconductive cap can be matched or substantially matched to the conductivity of the skin. For example, the electrical conductivity of the cap can be about 0.1 to 2 times the skin conductivity. The conductivity of each semiconductive cap can be matched so that about 5-30% (e.g., about 10%) of the RF energy is lost to the semiconductive cap. The conductivity of each semiconductive cap can be about 0.1 S/m at 1 MHz, which is about half of skin. The conductivity of the semiconductive caps can be graded such that the central and outer portions are more conductive than the inner portion.

If the electrical conductivity is exactly matched, then the current does not concentrate at the ceramic-tissue junction because, from an electrical perspective, no junction exists because of the matched conductivity values. The electrical conductivity for skin is about 0.22 S/m at 1 MHz RF frequency. In this case, the hot spot occurs at the metal electrode-ceramic interface, which, because of the ceramic's high thermal conductivity, is quickly diffused so that little heating occurs at the skin surface. However, RF energy is lost to the ceramic material and the amount of energy lost is proportional to the electrical conductivity value. In the typical ceramic geometries used, the loss of RF energy to ceramic can be as much as 50%. An electrical conductivity of 0.1 S/m at 1 MHz for the ceramic material can minimize this. Although not exactly matched to skin, the amount of RF energy lost to the ceramic material is around 10% while the thermal hotspot at the electrode edge is greatly diminished compared to when the ceramic material is not used.

Each semiconductive cap can include a semiconductive ceramic, which can have an electrical conductivity of about 0.03 S/m to about 3.0 S/m (e.g., about 0.05 S/m to about 0.3 S/m) and a thermal conductivity of about 5 W/m·° C. to about 500 W/m·° C. (e.g., about 50 to 250 W/m·° C.). The electrical conductivity can be about 0.1 S/m. The semiconductive cap can be a passive material in that material properties are independent of temperature. The shape of the cap is made such that the electrical pathlength through the semiconductive cap or ceramic material towards the edges of the electrodes are longer than toward the center. This passively increases the resistance for current flowing towards the edge compared to the center thereby better homogenizing the electric field at the tissue surface. This effectively spreads the current density leaving the probe over a larger area, which reduces the magnitude of the thermal hotspot.

Each semiconductive cap can include a conductive silicon carbide based ceramic doped with a nonconductive material and/or a nonconductive aluminum nitride based ceramic doped with a conductive material. The nonconductive material or the conductive material can be used to tune the cap to the desired conductivity.

A semiconductive cap can be formed by sintering silicon carbide. The ceramic can be prepared from a green preform, which can allow shaping of the electrode cap to the desired shape and can allow mixing of an additional material to tune the electrical conductivity of the finished product. Boron, aluminum and nitrogen are dopants that can be used to change the electrical conductivity of silicon carbide materials. In certain embodiments, the semiconductive cap is formed from AlN doped with $TiB_2$.

Each semiconductive cap need not be permanently attached to an electrode. Each semiconductive cap can be affixed, bonded or attached. Each semiconductive cap can be affixed to the respective electrode with a conductive epoxy. A silver conductive epoxy has good thermal and electrical properties, and can bond to metals, glasses and ceramics. Each semiconductive cap can have one or more surfaces metalized with copper, gold, silver or other materials so that the semiconductive cap can be soldered or brazed to the electrode.

Each semiconductive cap can be affixed to the respective electrode with a compressive tongue and groove joint. Each semiconductive cap can be affixed to the respective electrode with a screw passing through the cap and securing to the electrode. A compressive metal gasket can be used to improve thermal and electrical conduction between the cap and the electrode at the junction.

The source 74 can provide the RF energy at a frequency of about 100 kHz to about 10 MHz (e.g., about 1 MHz), although higher or lower frequencies can be used depending on the application. The source 74 can include a controller for the RF energy and/or a controller for the thermoelectric cooler 52. The source can provide the RF energy at about 10 J/cm$^3$ to about 500 J/cm$^3$ (e.g., about 50 J/cm$^3$ to about 120 J/cm$^3$), although higher or lower fluences can be used depending on the application. Using a volumetric heat capacity of 4 J/cm$^3$-° C. for skin, 120 J/cm$^3$ corresponds to a 30° C. rise in skin temperature. The source can provide the RF energy in pulses of about 0.1 second to about 1 second, although shorter or longer durations can be used depending on the application.

FIGS. 8A and 8B show a perspective view and a side view, respectively, of an electrode 22' and semiconductive cap 30', which can be used with base 18 shown in FIG. 6A. Electrode 22' can have a body portion 88, a tip 92 and a flange 96. Tip 92 can extend about 3.5 mm from body 88, and can be about 9 mm deep and 2 mm wide. Semiconductive cap 30' can define an opening, which is insertable over tip 92. Semiconductive cap 30' can abut flange 96 and be formed so that its outer surface is flush with the outer surface of the body portion 88 of the electrode 22'. Each semiconductive cap 30' can be permanently or semi-permanently attached to an electrode.

Cap 30' can have a variable thickness, e.g., a thickness between the blunt surface and the curved surface is thicker at an inner portion and thinner at a center portion to homogenize the electrical field at the skin surface. The variable thickness of cap 30' is symmetric. The cap 30' can be about 0.5 mm thick at the center and about 4.0 mm thick around its perimeter. The cap 30' can about 12 mm deep and 4 mm wide. The thickness of the wall surrounding the opening is about 1 mm in the x-plane and about 1.5 mm in the y-plane.

Figure 9A:
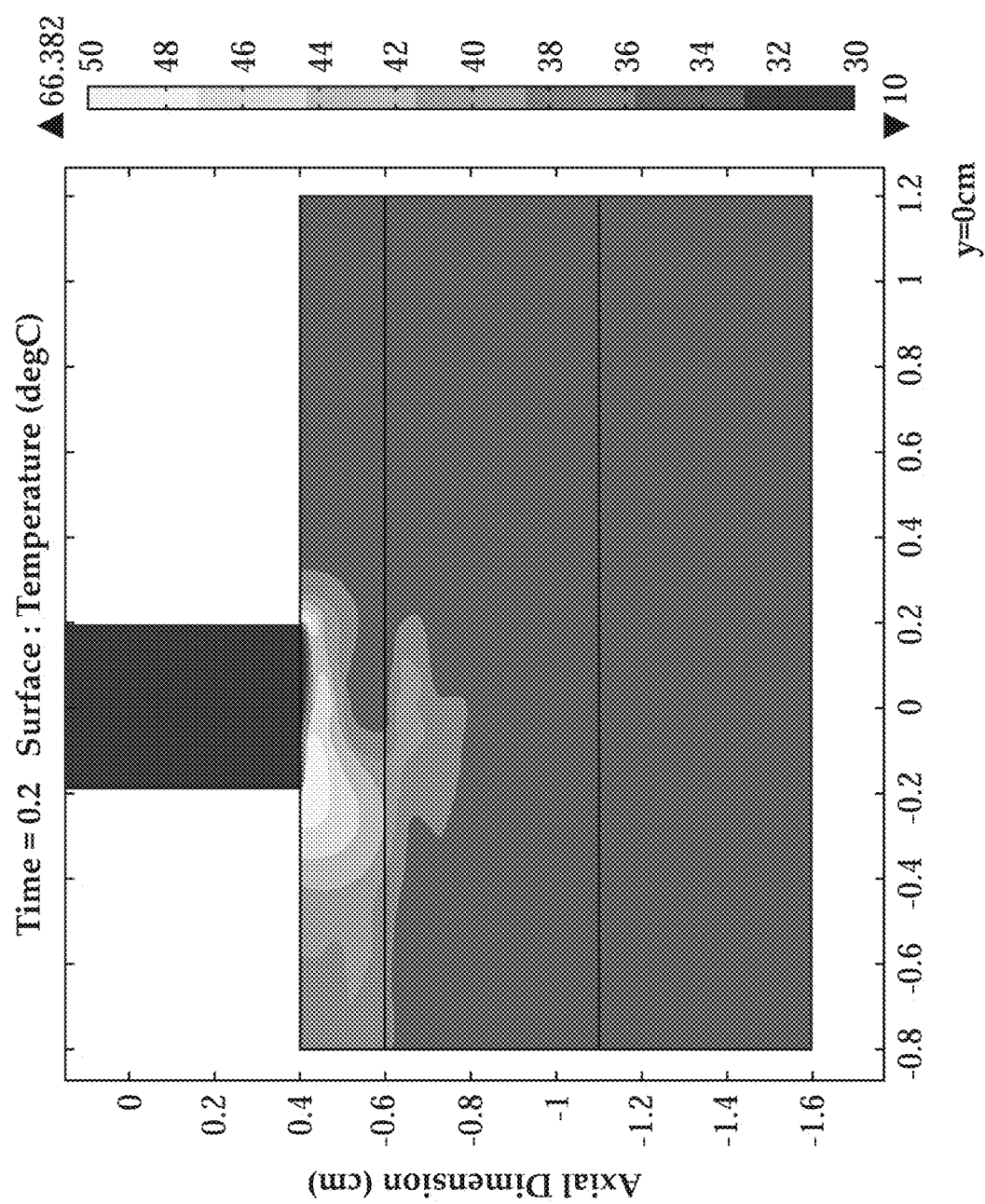
FIG. 9A shows a cross-section of a temperature profile in skin when using semiconductive caps having an elliptical shape.
Figure 9B:
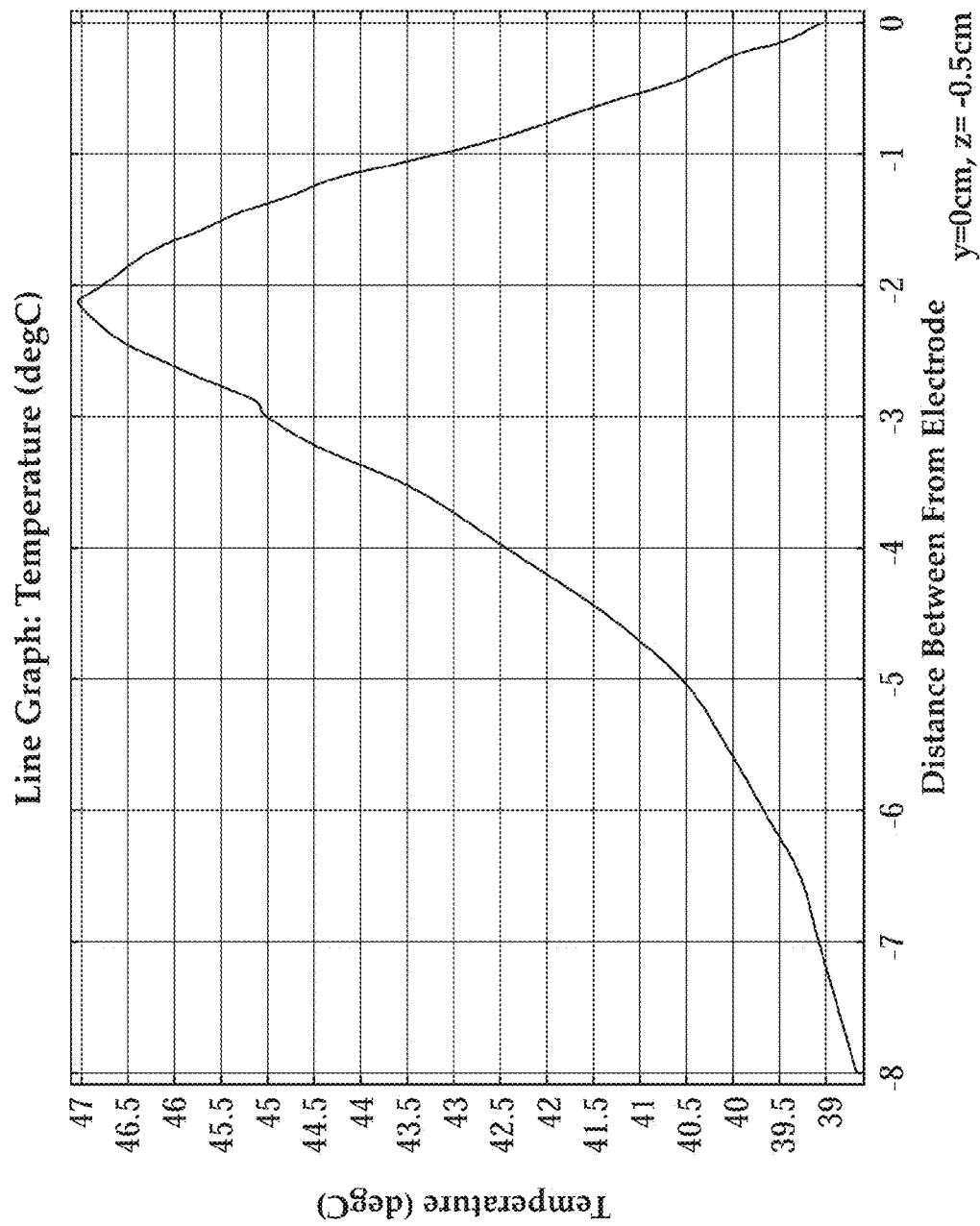
FIG. 9B shows temperature of the skin between electrodes.

FIG. 9A shows a cross-section of a temperature profile in skin when using semiconductive caps with a variable thickness. In the figure, a cap is illustrated, but the electrode is not. Each cap has a blunt surface in contact with the skin and a curved surface contacting the electrode. Each cap is elliptical or oval in shape. In this case, the hot zone around the edge is evenly distributed, with peak temperatures reaching about 69° C. (e.g., thermal hotspots remaining under 70° C.). FIG. 9B shows temperature of the skin between electrodes, with the temperature reaching a maximum about 2 mm from the electrode edge. In this configuration, a larger volume of tissue is heated compared to the previous configurations so the change in temperature is not as high even through more energy is being delivered to tissue.

Figure 10:
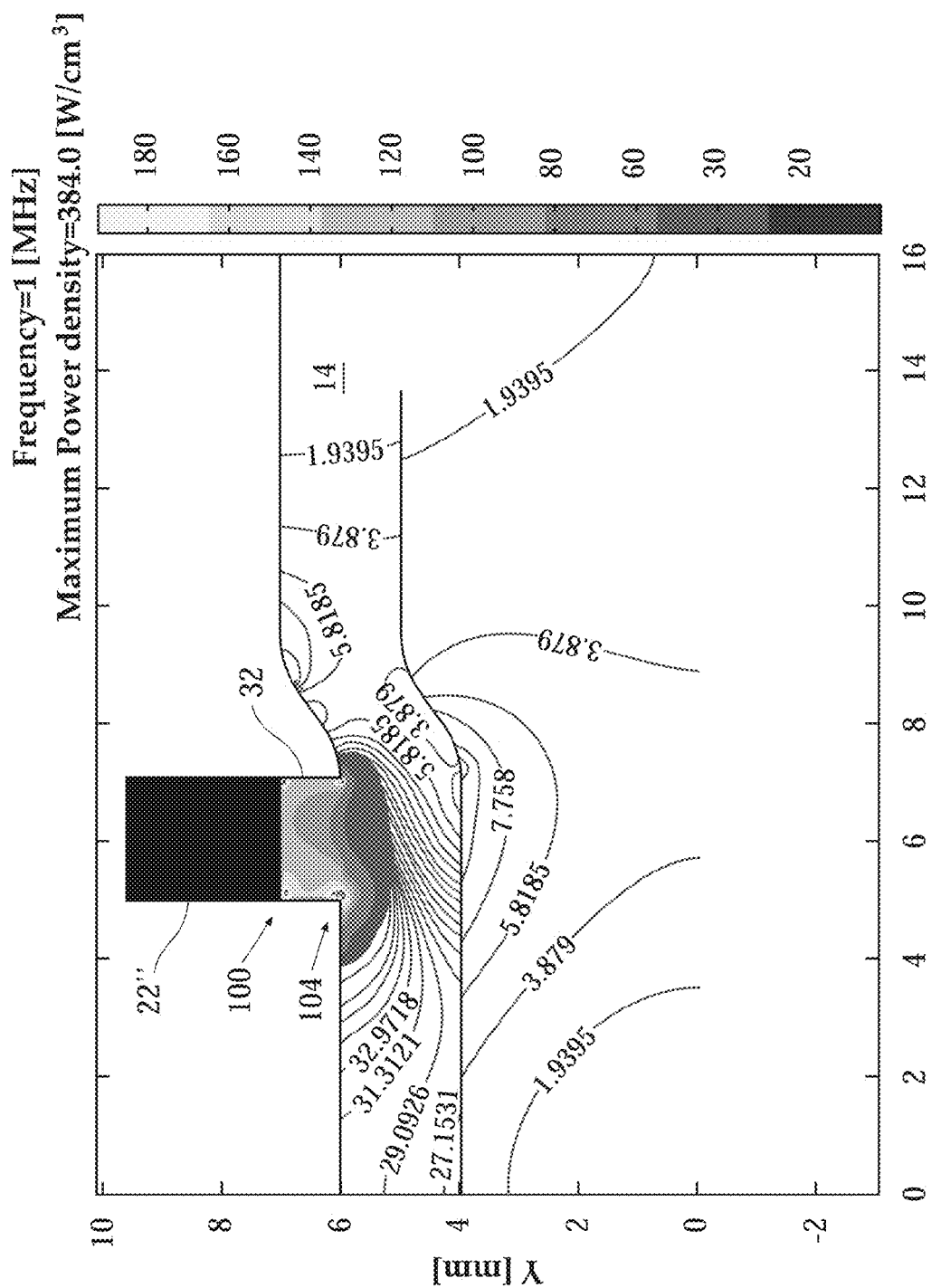
FIG. 10 shows RF power absorption for an electrode including a rectangular shaped cap.
Figure 11:
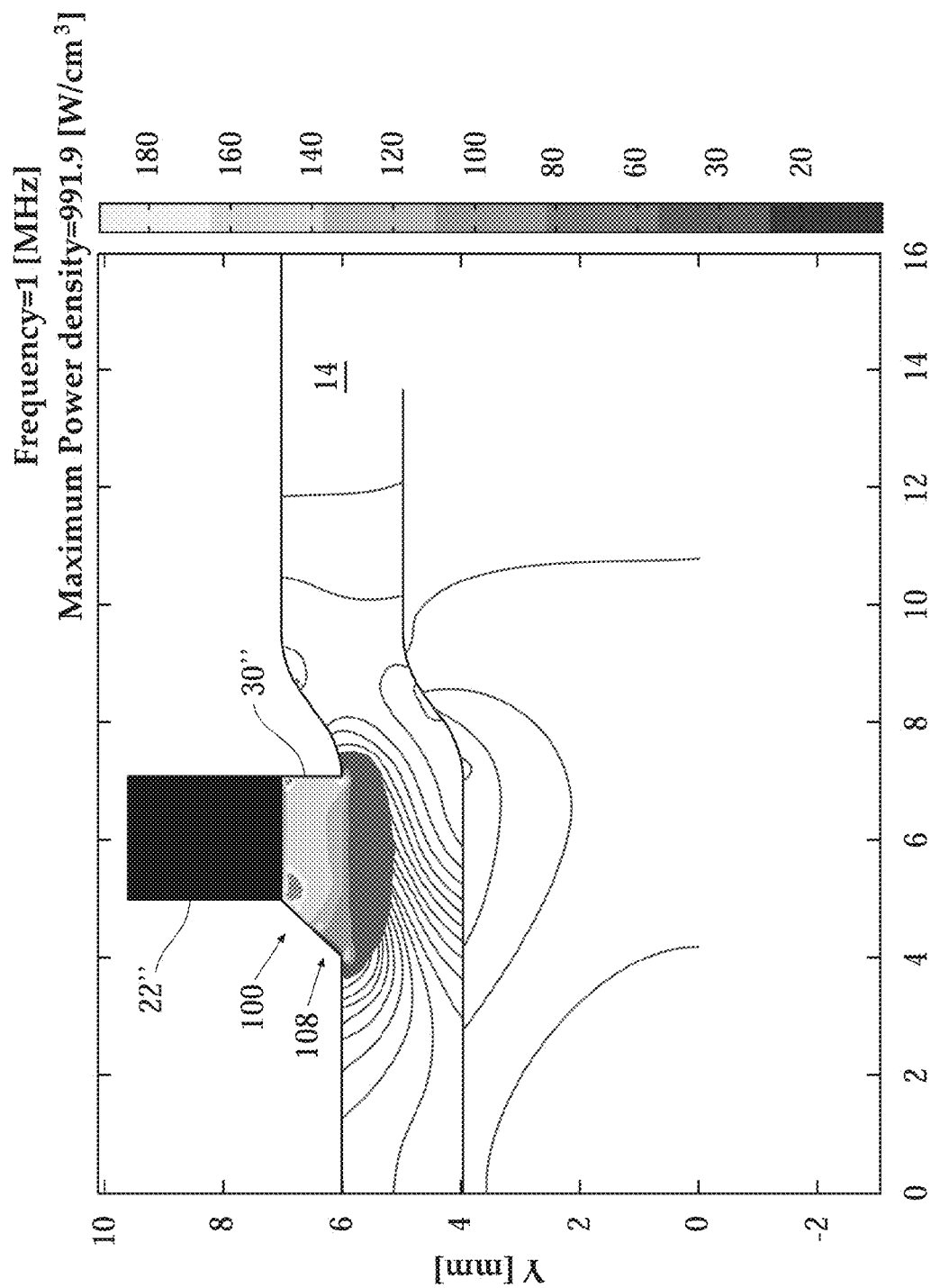
FIG. 11 shows RF power absorption for an electrode including a trapezoidal shaped cap.

FIG. 10 shows RF power absorption for an electrode 22" including a rectangular shaped cap 32, which has electrical conductivity matched to skin 14. While the hot spot 100 at the edge of the metal electrode is inside the cap, there is a hot spot 104 at the junction of the cap with the skin. Current is forced to fold around this corner, creating a high concentration there. Although much smaller than the hot spot without the semiconductive cap, the hot spot can be further reduced as shown in FIG. 11. The lines in FIG. 10 are power density contours in $W/cm^3$.

FIG. 11 shows RF power absorption for an electrode 22" including a trapezoidal shaped cap 30". A triangular section 108 of cap maintains the hot spot 100 inside the cap, but reduces or eliminates the hot spot 104 at the junction of the cap with the skin. The cap extends along the skin surface beyond the electrode edge. The cap extension tapers down towards the inner edge of the electrode.

Figure 12:
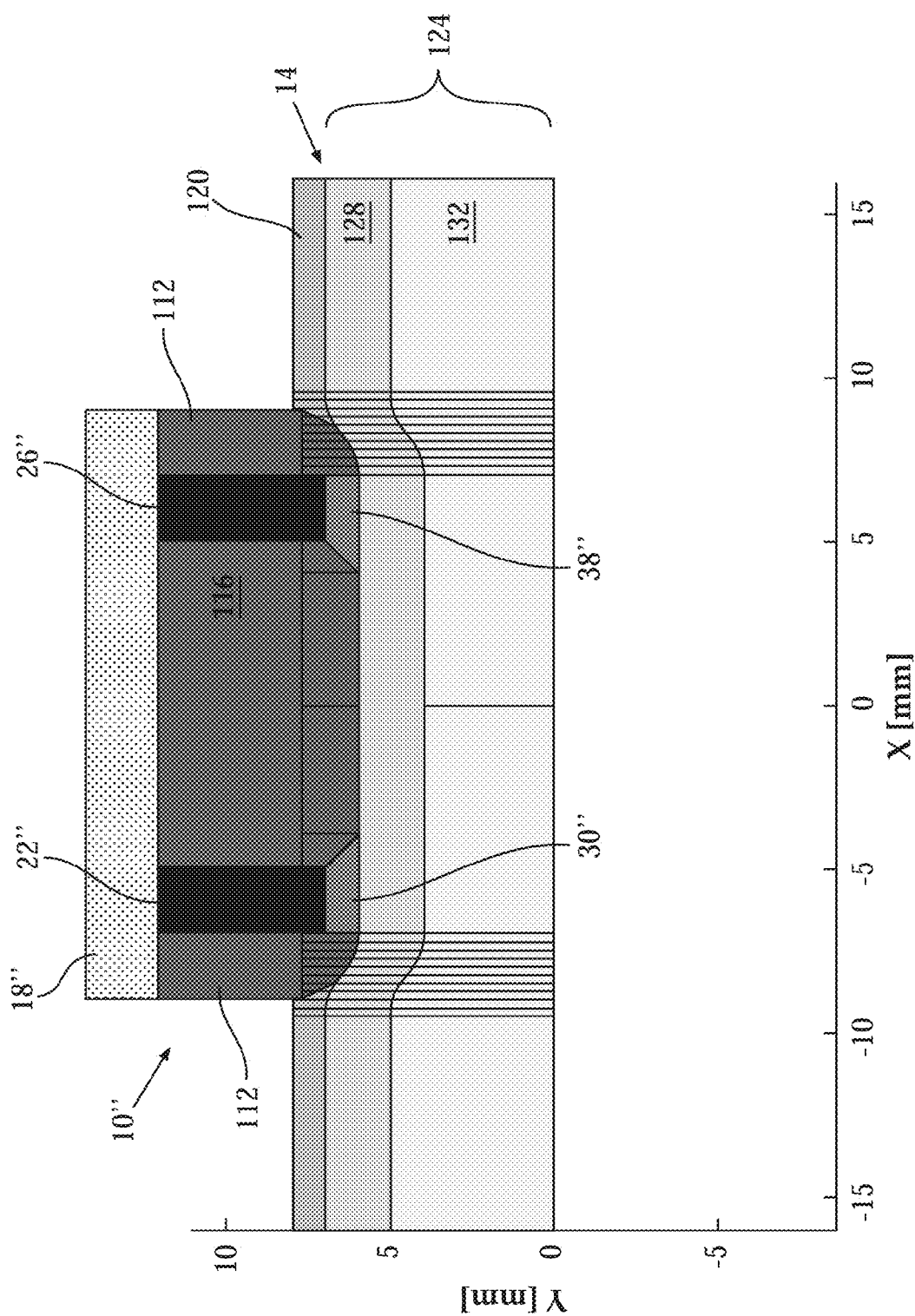
FIG. 12 shows a vertical cross-section of an applicator for RF energy.

FIG. 12 shows another embodiment of an applicator 10" for RF energy (monopolar or bipolar) delivered through a skin surface 14. The applicator 10" includes a base 18", a first electrode 22" connected to the base 18", a second electrode 26" connected to the base 18", a first semiconductive cap 30" disposed on a first distal end of the first electrode 22", a second semiconductive cap 38" disposed on a second distal end of the second electrode 26". The first electrode 22" extends from the base 18" toward a first location of the skin surface 14. The second electrode 26" extends from the base 18" toward a second location of the skin surface 14. The first electrode 22" is laterally offset along the skin surface 14 from the second electrode 26", and the first electrode 22" and the second electrode 26" have opposite phases. Each electrode 22" or 26" can be cooled to about 10° C. using a thermoelectric cooler. Each cap extends along the skin surface beyond the electrode edge. The cap extension tapers down towards the inner edge of the electrode.

The applicator 10" includes dielectric regions 112 and a waveguide 116 for delivering optical radiation to the skin. The skin surface 14 is shown in FIG. 11 as the interface between air 120 and the skin 124 comprising epidermal and dermal regions 128 and a subcutaneous fat region 132. The waveguide 116 can be coupled to a source of optical radiation, such as a laser or incoherent source.

In various embodiments, the optical source can produce radiation having a wavelength between about 250 nm and about 2,600 nm, although longer and shorter wavelengths can be used depending on the application. In some embodiments, the wavelength can be between about 400 nm and about 1,800 nm. In some embodiments, the wavelength can be between about 400 nm and about 1,100 nm. In some embodiments, the wavelength can be between about 1,160 nm and about 1,800 nm.

Figure 13:
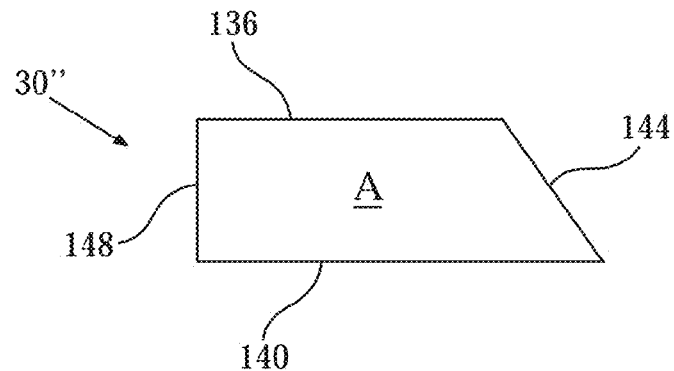
FIG. 13 shows an exploded view of a semiconductive cap.

FIG. 13 shows an exploded view of a semiconductive cap 30" or 38". The cap extends along the skin surface beyond the electrode edge. The cap extension tapers down towards the inner edge of the electrode. The cap can have a trapezoidal vertical cross-section including a first surface 136, a second surface 140 parallel or substantially parallel to the first surface 136, and a third surface 144 forming an obtuse angle A with the first surface 136, and a fourth surface 148. The second surface 140 is longer than the first surface 136. The second surface 140 is configured to contact the skin, and the first surface 136 is configured to adjoin a respective electrode.

Figure 14:
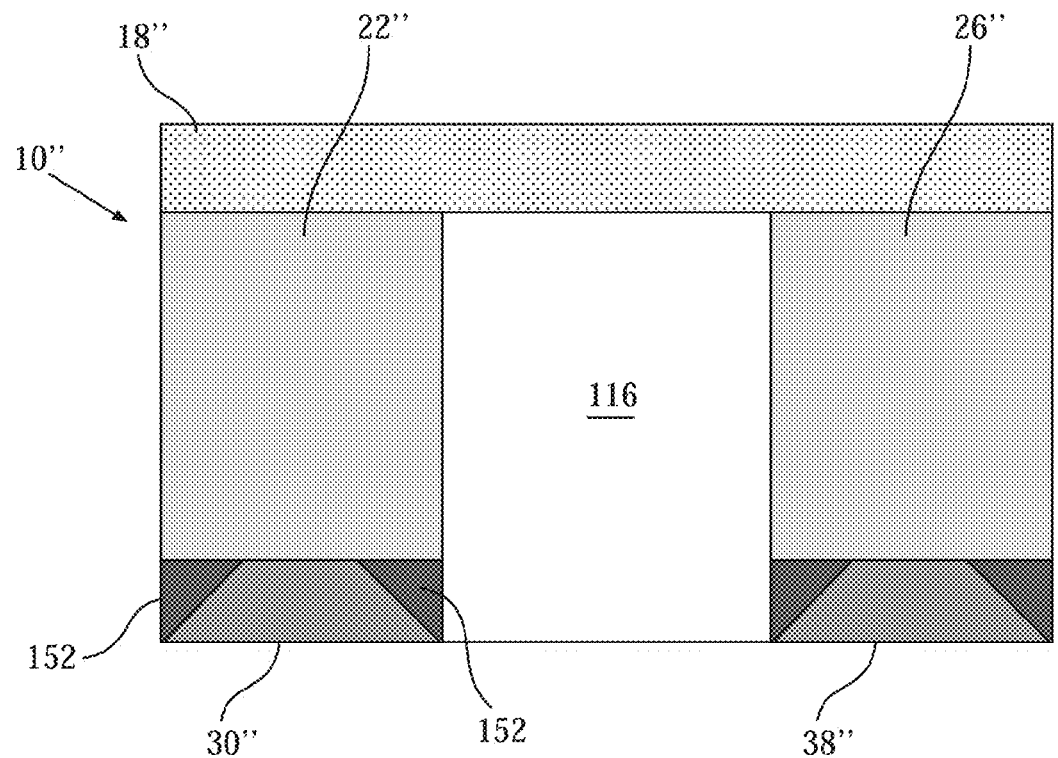
FIG. 14 a vertical cross-section of another applicator for RF energy.

FIG. 14 shows another embodiment of an applicator 10'" for RF energy delivered through a skin surface (not shown). The applicator 10'" includes a base 18", a first electrode 22" connected to the base 18", a second electrode 26" connected to the base 18", a first semiconductive cap 30'" disposed on a first distal end of the first electrode 22", a second semiconductive cap 38'" disposed on a second distal end of the second electrode 26". The first electrode 22" extends from the base 18" toward a first location of the skin surface. The second electrode 26" extends from the base 18" toward a second location of the skin surface. The first electrode 22" is laterally offset along the skin surface from the second electrode 26", and the first electrode 22" and the second electrode 26" have opposite phases. Each electrode 22" or 26" can be cooled to about 10° C. using a thermoelectric cooler.

The semiconductive caps 30'" and 38'" can be isosceles trapezoids or can have a cross-section as defined in FIG. 12. The cap(s) can extend along the skin surface, but need not extend beyond the electrode edges. Each cap extension can taper down towards either the inner or outer edge of the electrode, depending on the orientation of the extension.

The applicator 10'" includes a waveguide 116 for delivering optical radiation to the skin and electrically insulating regions 152. The waveguide 116 can be coupled to a source of optical radiation, such as a laser or incoherent source. The waveguide 116 can have a straight edge, as opposed to the notched profile shown in FIG. 11. Electrically insulating regions 152 can be used as fillers so that the hot spots occur inside the caps. The electrically insulating regions 152 can be formed from an insulating ceramic.

A semiconductive cap can be formed by combining a cap and insulating regions into one structure. For example, each semiconductive cap can include a conductive silicon carbide based ceramic doped with a nonconductive material in the insulating regions. Alternatively, each semiconductive cap can include a nonconductive aluminum nitride based ceramic doped with a conductive material in the semiconductive cap region. The nonconductive material or the conductive material can be used to tune portions of the cap to the desired conductivity. In certain embodiments, the semiconductive cap is formed from AlN that is doped with $TiB_2$ in the resistive region.

While the invention has been particularly shown and described with reference to specific illustrative embodiments, it should be understood that various changes in form and detail may be made without departing from the spirit and scope of the invention.

What is claimed is:

1. An applicator for RF energy delivered through a skin surface, comprising:
    a pair of electrodes connected to a base of the applicator and extending from the base toward a location of the skin surface, with each electrode having a distal end;
    a semiconductive cap affixed to the distal end of each electrode and constructed and arranged to contact the location of the skin surface,
    wherein each semiconductive cap is shaped such that an electrical path-length through the semiconductive cap towards edges of the associated electrode are longer than towards a center of the associated electrode.

2. The applicator according to claim 1, wherein each semiconductive cap comprises a semiconductive ceramic.

3. The applicator according to claim 2, wherein each semiconductive cap comprising the semiconductive ceramic comprises a conductive silicon carbide based ceramic doped with an electrical conductivity changing material, and wherein the electrical conductivity changing material is selected from the group consisting of boron, aluminum and nitrogen.

4. The applicator according to claim 2, wherein each semiconductive cap comprising the semiconductive ceramic comprises a nonconductive aluminum nitride based ceramic doped with a conductive material.

5. The applicator according to claim 1, wherein each semiconductor cap extends beyond the associated electrode and, in use, it extends along the skin surface beyond the associated electrode.

6. The applicator according to claim 1, further comprising a waveguide disposed between the pair of electrodes to deliver optical radiation.

7. The applicator according to claim 1, wherein each semiconductive cap extends beyond the edge of the associated electrode wherein, in use, it extends along the skin surface beyond the electrode edge and wherein each cap has a trapezoidal vertical cross-section including a first surface, a second surface parallel or substantially parallel to the first surface, a third surface forming an obtuse angle with the first surface, and a fourth surface.

8. The applicator according to claim 7, wherein the second surface is longer than the first surface and wherein the second surface is configured to, in use, contact the skin and the first surface is configured to adjoin the associated electrode.

9. The applicator according to claim 8, wherein the third surface abuts a surface of the waveguide.

10. The applicator according to claim 1, wherein each semiconductive cap has a curved surface that is in contact with the distal end of the associated electrode and that tapers from an inner edge to an outer edge of the semiconductive cap.

11. The applicator according to claim 1, wherein the shape of each semiconductive cap is such that resistance for electric current flowing towards the edges of the associated electrode is greater than that flowing towards the center of the associated electrode and wherein such current flow homogenizes an electric field at the skin surface and reduces magnitude of thermal hotspots.

* * * * *